United States Patent
Lawin et al.

[11] Patent Number: 6,051,714
[45] Date of Patent: Apr. 18, 2000

[54] PROCESSES FOR DECHLORINATING PYRIDINES

[75] Inventors: Phillip B. Lawin, Indianapolis, Ind.; Z. Jason Yang, Florence, S.C.; Gregory F. Hillstrom, Coatsville, Ind.; Michael P. Cruskie, Jr., Florence, S.C.

[73] Assignee: Reilly Industries, Inc., Indianapolis, Ind.

[21] Appl. No.: 09/267,004

[22] Filed: Mar. 12, 1999

Related U.S. Application Data

[60] Provisional application No. 60/077,816, Mar. 12, 1998.

[51] Int. Cl.$^7$ ....................... C07D 213/61; C07D 213/06
[52] U.S. Cl. ............................................. 546/345; 546/348
[58] Field of Search ....................... 546/345, 348

[56] References Cited

U.S. PATENT DOCUMENTS

| | | | |
|---|---|---|---|
| 3,732,230 | 5/1973 | Brewer et al. | 260/283 R |
| 4,108,856 | 8/1978 | Bowden et al. | 260/290 HL |
| 4,111,938 | 9/1978 | Redemann | 260/290 HL |
| 4,127,575 | 11/1978 | McGregor | 546/345 |
| 4,258,194 | 3/1981 | Weis et al. | 546/345 |
| 4,287,347 | 9/1981 | Fäh et al. | 546/345 |
| 4,563,531 | 1/1986 | Marinak et al. | 546/345 |
| 5,591,857 | 1/1997 | Friis et al. | 546/296 |

FOREIGN PATENT DOCUMENTS

| | | | |
|---|---|---|---|
| 0012117 | 12/1979 | European Pat. Off. | C07D 213/61 |
| 58-206564 | 12/1983 | Japan | C07D 213/61 |
| 63-275565 | 11/1988 | Japan | C07D 213/61 |
| 1-100158 | 4/1989 | Japan | C07D 213/61 |

*Primary Examiner*—Amelia Owens
*Attorney, Agent, or Firm*—Woodard, Emhardt, Naughton, Moriarty & McNett Patent and Trademark Attorneys

[57] ABSTRACT

Described are preferred processes for dechlorinating chlorinated pyridine compounds in the presence of zinc, an alkaline reagent and a phase transfer catalyst. Particularly preferred processes provide advantageous synthetic routes to 2,3,5-trichloropyridine starting with 2,3,5,6-tetrachloropyridine.

33 Claims, No Drawings

PROCESSES FOR DECHLORINATING PYRIDINES

REFERENCE TO RELATED APPLICATION

This application claims the benefit of U.S. provisional patent application Ser. No. 60/077,816 filed Mar. 12, 1998, which is hereby incorporated by reference herein in its entirety.

BACKGROUND

The present invention resides generally in the field of chlorinated pyridines. More particularly, the present invention relates in one preferred aspect to processes for preparing 2,3,5-trichloropyridine by dechlorinating 2,3,5,6-tetrachloropyridine.

As further background, polychlorinated pyridine derivatives are important intermediates in the preparation of pesticides. Consequently, much effort has been made at both the academic and industrial levels to find improved, economically-practicable processes for their preparation.

2,3,5-Trichloropyridine is one such intermediate. Proposed processes for its production have been widely diverse and have included both the selective chlorination of intermediate compounds, the selective dechlorination of higher-chlorinated pyridines, and other routes.

For example, 2,3,5-trichloropyridine can be prepared by reacting pyridine and phosphorous pentachloride as described by Sell et al., C. J. Chem. Soc. 73, 437 (1888). It can also be prepared by chlorinating pyridine hydrochloride with chlorine gas at 115° C.–120° C. as described by Sell, J. Chem. Soc. 93, 437 (1908). 2,3,5-Trichloropyridine can also be prepared by treating pyridine hydrochloride with liquid chlorine at 80° C. to 225° C. at an HCl pressure above 30 psig as disclosed in U.S. Pat. No. 3,732,230, or by the reaction of N-methyl-3,5-dichloro-2-pyridone with phosgene as taught in Ann. Chem. 486,71,78 (1931).

U.S. Pat. No. 4,108,856 discloses producing 2,3,5-trichloropyridine by reacting 3,5-dichloropyridine with chlorine at an elevated temperature in the range of 300° C. to 460° C. in the presence of a diluent such as chloroform or carbon tetrachloride. U.S. Pat. No. 4,287,347 discloses the production of 2,3,5-trichloropyridine by reacting 3,5-dichloro-2-pyridone with phosgene in the presence of certain N,N-disubstituted formamides and an inert solvent. 2,3,5-Trichloropyridine can also be produced by a liquid phase chlorination of 3,5-dichloro-2-trichloromethylpyridine at a temperature of 170° C. to 220° C. as taught in U.S. Pat. No. 4,563,531.

U.S. Pat. No. 4,111,938 reports that 2,3,5-trichloropyridine can be produced by reacting 2,3,5,6-tetrachloropyridine (Symtet) using zinc dust in a heterogeneous medium containing an alkaline reagent. The typical conditions of this '938 patent involve heating a mixture of about 1 equivalent of Symtet, 2 equivalents of zinc dust, 8 equivalents of aqueous sodium hydroxide (8N) and toluene at reflux for about 7 ours. U.S. Pat. No. 4,127,575 discloses a conversion of 2-hydrazino-3,5,6-trichloropyridine to 2,3,5-trichloropyridine using NaOCl as an oxidizing agent.

Symtet has also been converted to 2,3,5-trichloropyridine by hydrogenolysis using palladium on carbon as catalyst, as reported in JP 63275565. Reported conversion was very low, as was yield. U.S. Pat. No. 4,258,194 reports that 2,3,4,5-tetrachloropyridine can be converted to 2,3,5-trichloropyridine with zinc dust and ammonium salts of methane phosphonic acid monomethylester in methane phosphonic acid dimethylester. This method, however, failed to convert Symtet to 2,3,5-trichloropyridine.

Other routes to 2,3,5-trichloropyridine have also been reported, including the direct chlorination of 2-chloropyridine (JP 01100158) or 2,6-dichloropyridine (JP 58206564), and ring synthesis (EP 12117).

Despite the above-reported work, there remain needs for improved processes for the practicable, commercial-scale production of 2,3,5-trichloropyridine and other similar polychlorinated pyridines. The present invention is addressed to these needs.

SUMMARY OF THE INVENTION

The present invention features processes for dechlorinating chlorinated pyridines, especially to provide lower chlorinated pyridines. Preferred aspects of the invention involve the dechlorination of chlorinated pyridines with zinc in the presence of phase transfer catalysts and alkaline reagents.

Accordingly, in one preferred embodiment, the invention provides a process for dechlorinating a chlorinated pyridine compound, which includes conducting the dechlorination in the presence of zinc, a catalytic amount of a phase transfer catalyst, an aqueous base and a water immiscible organic solvent. Illustrative candidate syntheses to which this process may be applied include, for example, the dechlorination of 2,3,5,6-tetrachloropyridine to form 2,3,5-trichloropyridine and/or 2,5-dichloropyridine, the dechlorination of 2,3,4,5,6-pentachloropyridine to form 2,3,5,6-tetrachloropyridine and/or 2,3,5-trichloropyridine and/or 2,5-dichloropyridine, and the dechlorination of 2,3,4,5-tetrachloropyridine to form 2,3,5-trichloropyridine and/or 2,5-dichloropyridine.

In a particularly preferred embodiment, the invention provides a process for selectively preparing 2,3,5-trichloropyridine. This process includes dechlorinating 2,3,5,6-tetrachloropyridine to 2,3,5-trichloropyridine in the presence of zinc in a reaction medium including an aqueous base and a water-immiscible organic solvent. The medium also includes a phase transfer catalyst, desirably a cation of the formula:

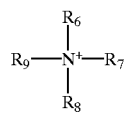

wherein:

$R_6$, $R_7$, and $R_8$, which may be the same as one another or may differ, are H; $C_1$ to $C_6$ alkyl, and wherein two of $R_6$, $R_7$ and $R_8$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and $R_9$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

In another preferred embodiment, the invention provides a process for preparing 2,3,5-trichloropyridine. This process includes reacting 2,3,5,6-tetrachloropyridine in the presence of zinc, an alkaline reagent, and a phase transfer catalyst to form 2,3,5-trichloropyridine.

The present invention provides improved processes for dechlorination of chlorinated pyridine derivatives, particularly for dechlorinating one or more of the 2-, 4-, and 6-positions of pyridines. In its most preferred aspects, the invention provides for the rapid, selective production of 2,3,5-trichloropyridine from 2,3,5,6-tetrachloropyridine. Additional preferred embodiments of the invention as well as their features and advantages will be apparent from the description that follows.

DESCRIPTION OF THE PREFERRED EMBODIMENTS

For the purposes of promoting an understanding of the principles of the invention, reference will now be made to certain of its embodiments and specific language will be used to describe the same. It will nevertheless be understood that no limitation of the scope of the invention is thereby intended, such alterations and modifications and applications of the principles of the invention as described herein being contemplated as would normally occur to one skilled in the art to which the invention pertains.

As disclosed above, the present invention features processes for dechlorinating chlorinated pyridines, particularly to provide lower chlorinated pyridines. Preferred aspects of the invention involve dechlorinations of polychlorinated pyridines in the presence of zinc, a phase transfer catalyst, and an alkaline reagent. In particular aspects of the invention, provided are processes for dechlorinating one or more of the 2-, 4- and 6-positions of chlorinated pyridines.

In a general sense, the starting materials for processes of the invention will be encompassed by the formula:

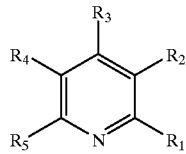

wherein
$R_1$, $R_2$, $R_3$, $R_4$, and $R_5$ are H, chloro, or a non-interfering substituent such as a $C_1$ to $C_{20}$ hydrocarbon, e.g. alkyl, with the proviso that at least one of $R_1$, $R_2$, $R_3$, $R_4$ and $R_5$ is chloro. It is preferred that the starting chlorinated pyridine compound be a polychloro-pyridine compound, and thus that at least two of $R_1$, $R_2$, $R_3$, $R_4$, and $R_5$ are chloro. Illustrative starting materials thus include, for example, 2,3,4,5,6-pentachloropyridine, tetrachloropyridine compounds such as 2,3,5,6-tetrachloropyridine, optionally substituted at the 4-position with a non-interfering substituent as disclosed above, especially lower ($C_1$ to $C_6$) alkyl, and 2,3,4,5-tetrachloropyridine, optionally substituted at the 6-position with a non-interfering substituent as disclosed above, especially lower alkyl.

An especially preferred feature of the invention involves the discovery that 2,3,5,6-tetrachloropyridine can be rapidly and selectively converted to 2,3,5-trichloropyridine in good yield by dechlorination in the presence of zinc and a phase transfer catalyst in a reaction medium including an inert organic solvent and an aqueous alkaline reagent. The preferred starting material, 2,3,5,6-tetrachloropyridine

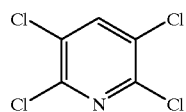

can be obtained commercially or can be prepared using procedures well known to the art and literature. For example, suitable processes by which 2,3,5,6-tetrachloropyridine can be made are disclosed in U.S. Pat. No. 5,591,857 issued Jan. 7, 1997 and the background literature discussed therein. As will be appreciated, this and other polychlorinated pyridine starting materials may be obtained from these or other known sources or chemical routes without departing from the present invention.

Other illustrative syntheses to which the present invention may be applied include other syntheses which involve the dechlorination of one or more of the 2-, 4- and 6-positions of chlorinated pyridines. For example, the invention may be applied to the production of 2,3,5-trichloropyridine and/or 2,3,5,6-tetrachloropyridine by the dechlorination of 2,3,4,5,6-pentachloropyridine, or the production of 2,3,5-trichloropyridine by the dechlorination of 2,3,4,5-tetrachloropyridine.

The selected chlorinated pyridine starting material is dechlorinated in the presence of zinc as an electron donor. It is preferred that the zinc be used in particulate form to provide increased surface area for the reaction. Zinc chips or zinc dust may be used. As to amounts, it is preferred that at least 0.5 gram atoms of zinc be used per gram atom of chlorine to be removed. Typically, about 0.5 gram atoms to 3 gram atoms of zinc will be used per gram atom of chlorine to be removed, more preferably about 1 to 3 gram atoms of zinc per gram atom of chlorine. Thus, as an example, in the case of the dechlorination of 2,3,5,6-tetrachloropyridine to 2,3,5-trichloropyridine, it will be preferred to use about 0.5 to about 3 gram atoms of zinc per mole of 2,3,5,6-tetrachloropyridine. Most preferably in this case, about 1 to about 1.5 gram atoms of zinc are used per mole of 2,3,5,6-tetrachloropyridine.

The preferred phase transfer catalyst will demonstrate the capacity to increase the rate of reaction to form the desired dechlorinated pyridine derivative. Preferred phase transfer catalysts include organic quaternary ammonium compounds. For example, the phase transfer catalyst can be provided by a cation encompassed by the formula:

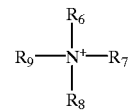

wherein:
$R_6$, $R_7$, and $R_8$, which may be the same as one another or may differ, are H; $C_1$ to $C_6$ alkyl, and wherein two of $R_6$, $R_7$ and $R_8$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and $R_9$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

Within this formula, it is preferred that $R_6$, $R_7$, $R_8$, and $R_9$ all be organic (i.e. not H), and particularly preferred that they be alkyl, and most preferably $C_1$ to $C_4$ alkyl.

These preferred phase transfer catalysts can be provided to the reaction mixture by a suitable salt, for example of the formula:

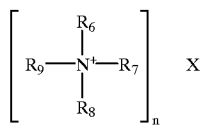

wherein $R_6$, $R_7$, $R_8$, and $R_9$ are as defined above, X is an anion having from 1 to 3 negative charges, and n is 1 to 3 and corresponds to the number of negative charges of X. Preferred anions, X, include halogens and hydroxy groups.

Other phase transfer catalysts may also be used, alone or in combination. For example, suitable phase transfer catalysts include quaternary-forms of cyclic amines, e.g. N,N-dimethylpyrrolidinium salts, quaternary forms of diamines, e.g. diamine methyl quats such as ethylene diamine methyl quat, and the like. Still further compounds useful as phase transfer catalysts in the invention include alcohols (including lower alkanols and longer-chain aliphatic alcohols), ethers (e.g. crown ethers), polyethers such as polyethylene glycol (PEG) of differing molecular weights, and other like compounds.

It has been found that the provision of such phase transfer catalysts to the reaction mixture facilitates an increase in the rate of reaction, and also advantageously eliminates undesired clumping of particulate zinc, such as zinc dust, during the reaction procedure.

As to amounts, it is preferred that the phase transfer catalysts be charged generally in catalytic amount. As used in the art and herein, the term catalytic amount contemplates amounts which are less than stoichiometric relative to the relevant reactant (chlorinated pyridine compound). In the present invention, the phase transfer catalyst will usually be used in the range of about 0.01 mole percent to 30 mole percent relative to the 2,3,5,6-tetrachloropyridine or other chlorinated pyridine starting material. Most preferably, the phase transfer catalyst is charged in an amount of about 0.05 mole percent to about 10 mole percent relative to the polychlorinated pyridine starting material.

A variety of alkaline reagents can be used in the present invention. Generally, the alkaline reagent utilized will be sufficient to maintain a mixture at a pH of at least 10, and preferably falling within the range of about 12 to 14. Aqueous alkali metal hydroxides, aqueous alkaline earth metal hydroxides, and aqueous ammonium hydroxide are preferred, with aqueous sodium hydroxide providing a convenient, effective source of alkaline reagent and therefore being most preferred. When used, it is preferred that the aqueous NaOH have a concentration of about 10% w/w to about 40% w/w, more preferably about 20% w/w to about 30% w/w.

The water-immiscible organic solvent utilized can be selected from a variety of known organic solvents. Suitable solvents include for example inert aliphatic solvents such as hexane, heptane, haloalkanes such as perchloroethylene or methylene chloride, and the like, and inert aromatic solvents such as benzene or alkyl benzene solvents including toluene, xylene, ethyl benzene, 2-chlorotoluene, as well as other benzene derivatives such as alkoxy benzenes, e.g. anisole. Preferred among these are aromatic solvents, more preferably toluene, mixed xylenes, or ortho-xylene.

Discussing now the procedures involved in the conduct of preferred inventive reactions, the reactants and solvent(s) can be charged all together prior to reacting, or one or more of the materials such as the zinc, phase transfer catalyst, or base can be all or partially dosed to the reaction mixture over the course of the reaction. For example, in one preferred mode, processes of the invention are carried out while adding a portion of the zinc at the start of the procedure, and then periodically dosing the remainder of the zinc to the reaction mixture over the course of the reaction. This has been found to be helpful in controlling the exotherm produced by the reaction and thus also the selectivity to the desired product, particularly in the production of 2,3,5-trichloropyridine from 2,3,5,6-tetrachloropyridine. This and similar variations will be apparent to the skilled artisan upon reviewing the disclosures herein.

As to temperature, preferred reactions of the invention are conducted at temperatures in the range of about 10° C. to about 100° C. More preferably, these temperatures are in the range of about 20° C. to about 70° C. The reactions may be allowed to proceed adiabatically, and when so conducted the reaction exotherm will cause a rise in temperature over the course of the reaction. The reactions may also be conducted under isothermal conditions, with appropriate measures taken to remove heat generated by the exotherm. Relatedly, the reaction pressure utilized can generally be subatmospheric, atmospheric, or superatmospheric. As to duration, preferred inventive reactions will typically be complete in about 0.5 to about 24 hours, more preferably in the range of 1 to about 10 hours.

Reactions in accordance with the invention are preferably conducted with agitation of the reactor contents, for example by stirring. This assists in increasing the reaction rate and in preventing the undesired agglomeration of zinc particles.

As to results, preferred processes of the invention provide high yields of the dechlorinated pyridine product, particularly 2,3,5-trichloropyridine from 2,3,5,6-tetrachloropyridine, generally in excess of 60% isolated yields. In addition, chemical yields are readily in excess of 70% based on GC analysis. Also advantageously, preferred processes of the invention provide high selectivity to the desired dechlorinated pyridine. For example, 2,3,5-trichloropyridine can be produced in a selectivity above about 80% in more preferred processes.

Reacted mixtures of the invention can be worked up using general procedures known to the art. It is noted that upon completion of the reaction, there sometimes can occur a layer of agglomerated solids which can be filtered during workup. Layer separations, when needed, can be conducted in a conventional manner, with the chlorinated pyridine product generally occurring in the organic layer. After separation, such layer can be conventionally processed to obtain the chlorinated pyridine product in a purified form, for example by fractional distillation to achieve a purity of about 95% or greater.

The purified polychlorinated pyridine products in the invention can be used in a conventional manner, and are known intermediates to pesticides and other useful compounds.

In order to provide a further understanding of the invention and its advantages, the following specific examples are provided. It will be understood that these examples are illustrative and not limiting of the invention.

EXAMPLE 1

To a 5000 mL round-bottom flask fitted with a thermometer and a mechanical stirrer were added 2,3,5,6-tetrachloropyridine (217 g, 1 mole) and benzene (500 mL). Sodium hydroxide solution (8 N, 1000 mL, 8 mole), tetramethylammonium bromide (1.5 g) and zinc dust (140 g, 2.1 mole) were then successively added to the above solution, providing a heterogeneous reaction medium. The resulting gray suspension was stirred at ambient temperature and the course of the reaction monitored by gas-liquid chromatography. The reaction was exothermic as the temperature rose slowly to around 47° C. after about an hour. After reacting for 3 hours, the chemical yield of and selectivity for 2,3,5-trichloropyridine were 77% and 80%, respectively, based on GC analysis, with the reaction mixture containing lower amounts of other chloropyridines including 2,5-dichloropyridine, 3,5-dichloropyridine and 2,3,6-trichloropyridine. The reacted mixture was filtered and the two layers of the filtrate were separated by separational funnel. The benzene layer was evaporated at reduced pressure to give the crude product as a yellow oil which solidified upon standing. The crude mixture was subject to fractional distillation at 25 mmHg, resulting in an isolated yield of 2,3,5-trichloropyridine of 70%.

EXAMPLE 2 (COMPARATIVE)

To a 500 mL round-bottom flask fitted with a thermometer and a magnetic stirrer were added 2,3,5,6-tetrachloropyridine (21.7 g, 0.1 mole) and benzene (50 mL). Sodium hydroxide solution (8 N, 100 mL, 0.8 mole) and zinc dust (14 g, 0.21 mole) were then successively added to the above solution. The resulting gray suspension was heated at reflux for 7 h. The chemical yield of and selectivity for 2,3,5-trichloropyridine were 28% and 46%, respectively, based on GC analysis.

EXAMPLE 3

A 3000 mL, four neck round bottom flask was equipped with a mechanical stirrer, thermometer, reflux condenser, and an opening for the addition of zinc dust. The flask was charged with ortho-xylene (630.4 g, 725 mL) followed by the addition of 2,3,5,6-tetrachloropyridine (525 g, 2.42 mole). Agitation was started and water (775.1 g, 775 mL), 50% NaOH (1162.7 g, 765 mL), and 25% tetramethylammonium hydroxide (5.2 g) were added to the flask. The reaction mixture was heated to 50° C. and zinc dust (195.0 g, 2.98 mole) was added, in equal portions, over a 5-hour period while holding the temperature between 55–60° C. The reaction mixture was then heated at 55–60° C. for an additional 5 hours. After the reaction, the layers were allowed to separate and the top layer (organics) was filtered. Hydrochloric acid (32%, 750.2 g) was added to the bottom layer which was then heated under reflux for 5 hours to convert unreacted zinc to zinc hydroxide (the zinc hydroxide can subsequently be isolated by filtration for recycle value). Organics present in the bottom layer were removed by steam distillation during this time using a Dean-Stark trap, and added to the organics layer. Fractional distillation of the organics layer gave an isolated yield of 2,3,5-trichloropyridine of 65%.

EXAMPLES 4–13

A number of runs were performed in a similar manner as that described in Example 1, as outlined in Table 1. The organics layer was separated and sampled for GC analysis. The results are set forth in Table 1, in which the following abbreviations appear: Symtet=2,3,5,6-tetrachloropyridine; Solv=solvent; Cat=catalyst; Temp=temperature; Sel=selectivity for 2,3,5-trichloropyridine; TMAH=tetramethylammonium hydroxide; TMAB=tetramethylammonium bromide; PEG300=polyethylene glycol, M.W. 300); BTMAC=benzyltrimethylammonium chloride; DDMA=diallyldimethylammonium chloride; DMP=dimethylpyrrolidinium iodide; 18-C-6=18-crown-6-ether.

TABLE 1

| Ex. | Symtet (moles) | Solv (mL) | NaOH (moles) | Cat (moles) | Zn (moles) | Temp (° C.) | Sel | Yield |
|---|---|---|---|---|---|---|---|---|
| 4 | 0.6 | Toluene (180) | 3.0 | TMAB (0.0065) | 0.84 | 50 | 84% | 79% |
| 5 | 0.6 | Hexane (180) | 3.0 | TMAH (0.0066) | 0.72 | 60 | 82% | 68% |
| 6 | 0.6 | o-xylene (180) | 3.6 | Zn(OH)$_2$ (0.1) | 0.72 | 55–65 | 88% | 71% |
| 7 | 0.6 | Toluene (200) | 3.6 | PEG300 (0.01) | 0.84 | 40–70 | 86% | 65% |
| 8 | 0.1 | Toluene (50) | 0.8 | BTMAC (0.0006) | 0.20 | 40–50 | 73% | 73% |
| 9 | 0.23 | Toluene (60) | 1.4 | 18-C-6 (0.00023) | 0.28 | 55–60 | 81% | 67% |
| 10 | 0.14 | Toluene (40) | 0.8 | Ethanol (0.028) | 0.17 | 50–55 | 93% | 55% |
| 11 | 0.1 | Toluene (50) | 0.5 | DDMA (0.0041) | 0.14 | 60 | 82% | 57% |
| 12 | 0.1 | Toluene (50) | 0.5 | DMP (0.0044) | 0.14 | 60 | 68% | 62% |
| 13 | 0.1 | Toluene (50) | 0.5 | TMAH (0.00011) + PEG300 (0.001) | 0.12 | 55-60 | 80% | 72% |

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. In addition, all publications cited herein are indicative of the level of skill in the art and are hereby incorporated by reference in their entirety as if each had been individually incorporated by reference and fully set forth.

What is claimed is:

1. A process for preparing 2,3,5-trichloropyridine, comprising:
   reacting 2,3,5,6-tetrachloropyridine in a reaction medium including zinc, an aqueous alkaline reagent, a water-immiscible organic solvent, and a phase transfer catalyst to form 2,3,5-trichloropyridine.

2. The process of claim 1, wherein the phase transfer catalyst includes a cation of the formula:

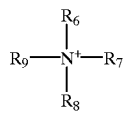

wherein:
   $R_6$, $R_7$, and $R_8$, which may be the same as one another or may differ, are H; $C_1$ to $C_6$ alkyl, and wherein two of $R_6$, $R_7$ and $R_8$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and
   $R_9$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

3. The process of claim 1, wherein the aqueous alkaline reagent is an aqueous alkali or alkaline earth metal hydroxide, or aqueous ammonium hydroxide.

4. The process of claim 1, wherein the water-immiscible organic solvent is an aromatic solvent.

5. The process of claim 4 wherein the aromatic solvent is benzene or an alkylbenzene solvent.

6. The process of claim 5 wherein the aromatic solvent is toluene.

7. The process of claim 5 wherein the aromatic solvent is ortho-xylene.

8. The process of claim 1, wherein said zinc is included in a ratio of at least about 0.5 gram atoms per mole of said 2,3,4,5-tetrachloropyridine.

9. The process of claim 8, wherein said zinc is included in a ratio of about 0.5 to about 3 gram atoms per mole of said 2,3,4,5-tetrachloropyridine.

10. The process of claim 2, wherein $R_6$, $R_7$, and $R_8$ are each $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

11. The process of claim 10, wherein $R_6$, $R_7$, $R_8$, and $R_9$ are $C_1$ to $C_6$ alkyl.

12. The process of claim 11, wherein $R_6$, $R_7$, $R_8$, and $R_9$ are each methyl.

13. The process of claim 11, wherein said dechlorinating is conducted at a temperature in the range of about 10° C. to about 100° C.

14. The process of claim 1, wherein said phase transfer catalyst is present in an amount of about 0.01 mole % to about 30 mole % relative to said 2,3,5,6-tetrachloropyridine.

15. The process of claim 14, wherein said aqueous alkaline reagent is aqueous sodium hydroxide.

16. The process of claim 15, wherein said aqueous alkaline reagent is about 10% w/w to about 40% w/w aqueous sodium hydroxide.

17. The process of claim 1, wherein said reacting is conducted under adiabatic temperature conditions.

18. The process of claim 1, wherein said dechlorinating is conducted under isothermal temperature conditions.

19. The process of claim 1, wherein said zinc, phase transfer catalyst, or aqueous alkaline reagent is added to said reaction mixture in multiple doses over the course of said reacting.

20. A process for dechlorinating a chlorinated pyridine compound, comprising:
   dechlorinating a chlorinated pyridine compound in a reaction medium including zinc, an aqueous alkaline reagent, a water-immiscible organic solvent, and a catalytic amount of a phase transfer catalyst.

21. The process of claim 20, wherein the phase transfer catalyst has a cation of the formula:

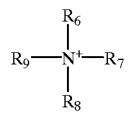

wherein:
   $R_6$, $R_7$, and $R_8$, which may be the same as one another or may differ, are H; $C_1$ to $C_6$ alkyl, and wherein two of $R_6$, $R_7$ and $R_8$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and
   $R_9$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

22. The process of claim 20 or 21, which comprises dechlorinating 2,3,5,6-tetrachloropyridine to form 2,3,5-trichloropyridine.

23. The process of claim 20 or 21, which comprises dechlorinating 2,3,4,5-tetrachloropyridine to form 2,3,5-trichloropyridine.

24. The process of claim 20 or 21, which comprises dechlorinating 2,3,4,5,6-pentachloropyridine to form 2,3,5,6-tetrachloropyridine.

25. The process of claim 20 or 21, which comprises dechlorinating 2,3,4,5,6-pentachloropyridine to form 2,3,5-trichloropyridine.

26. The process of claim 20 or 21, which comprises dechlorinating 2,3,4,5,6-pentachloropyridine to form 2,5-dichloropyridine.

27. The process of claim 20 or 21, which comprises dechlorinating 2,3,5,6-tetrachloropyridine to form 2,5-dichloropyridine.

28. The process of claim 20 or 21, which comprises dechlorinating 2,3,4,5-tetrachloropyridine to form 2,5-dichloropyridine.

29. A dechlorination process, comprising dechlorinating a pyridine compound of the formula:

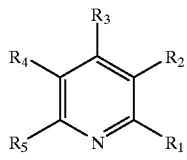

wherein $R_1$, $R_2$, $R_3$, $R_4$, and $R_5$ are H, chloro, or a $C_1$ to $C_{20}$ hydrocarbon group, with the proviso that at least one of $R_1$, $R_2$, $R_3$, $R_4$, and $R_5$ is chloro, in the presence of zinc, an aqueous alkaline reagent, a water-immiscible organic solvent, and a catalytic amount of a phase transfer catalyst.

30. The process of claim 26, wherein said dechlorinating is conducted with about 0.01 mole % to about 30 mole % of said phase transfer catalyst relative to said pyridine compound.

31. The process of claim 27, wherein said water-immiscible organic solvent is an inert aromatic solvent or inert aliphatic solvent.

32. The process of claim 28, wherein said pyridine compound is selected from the group consisting of 2,3,4,5,6-pentachloropyridine, 2,3,5,6-tetrachloropyridine, and 2,3,4,5-tetrachloropyridine.

33. The process of claim 29, wherein said pyridine compound is 2,3,5,6-tetrachloropyridine.

* * * * *